US00PP37787P2

(12) United States Plant Patent
Piston

(10) Patent No.: US PP37,787 P2
(45) Date of Patent: Oct. 20, 2026

(54) STRAWBERRY PLANT NAMED 'DUNA'

(50) Latin Name: ***Fragaria* x *ananassa***
Varietal Denomination: DUNA

(71) Applicant: Fresas Nuevos Materiales S.A., Huelva (ES)

(72) Inventor: Fernando Piston, Huelva (ES)

(73) Assignee: Fresas Nuevos Materiales S.A., Huelva (ES)

( * ) Notice: Subject to any disclaimer, the term of this patent is extended or adjusted under 35 U.S.C. 154(b) by 0 days.

(21) Appl. No.: 19/319,517

(22) Filed: Sep. 4, 2025

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./208, 209
See application file for complete search history.

(56) References Cited

U.S. PATENT DOCUMENTS

PP26,709 P3 * 5/2016 Larson ..... A01H 5/08
Plt./208

OTHER PUBLICATIONS https://in.linkedin.com/company/fresasnm (found online Nov. 18, 2025) (Year: 2025).*
International Union for the Protection of New Varieties of Plants, Strawberry, UPOV Code: FRAGA, Guidelines for the Conduct of Tests for Distinctness, Uniformity and Stability, 22/11, Aug. 31, 2023, 40 pages.

* cited by examiner

*Primary Examiner* — Susan McCormick Ewoldt
*Assistant Examiner* — Zachariah Allan Kay
(74) *Attorney, Agent, or Firm* — COOLEY LLP

(57) ABSTRACT

The present invention provides a new and distinct strawberry plant designated as 'DUNA', which originated from seed produced by manual cross between 'E70' and '25'. The new strawberry is a short-day with a long, conical, glossy and a light red colored fruit. This new strawberry is characterized by a fruit of excellent quality, long shelf-life and high value of Brix degrees.

7 Drawing Sheets

Botanical designation: *Fragaria*x*ananassa*.
Varietal denomination: 'DUNA'.

BACKGROUND OF THE INVENTION

The present invention relates to a new and distinct short-day strawberry variety designated as 'A18-65-4' by the breeder, and later named 'DUNA'.

SUMMARY OF THE INVENTION

The present invention relates to a new and distinct strawberry variety. The varietal denomination of the new variety is 'DUNA'. Among the characteristics which are believed to distinguish the new variety from other varieties are a combination of traits which include the day length that is a short-day; the plant has a medium vigor and high yield with very early harvest of fruits; the fruit color is medium red; and the fruit size is large. The 'DUNA' strawberry plant is tolerant to *Sphaerotheca macularis* (the causal agent of powdery mildew, *Phytophthora cactorum* (the causal agent of crown rot), and *Macrophomina phaseolina* (the causal agent of charcoal rot).

'DUNA' was created in a breeding program and is the result of a controlled-cross between two parental lines—the female experimental strawberry variety designated 'E70' and the male experimental strawberry variety designated 'E25', made by the Inventor and was first fruited growing fields in Huelva, Spain. From the beginning and during testing, the plant was designated 'A18-65-4.'

This new variety was asexually reproduced via runners (stolons) by the inventor at Huelva, Spain. Asexual propagules from the original source have been tested in Huelva, Spain growing fields and to a limited extent, secondary grower fields in high elevation. The properties of this variety were found to be transmissible by such asexual reproduction. This cultivar is stable and reproduces true to type in successive generations of asexual reproduction.

BRIEF DESCRIPTION OF THE DRAWING

The accompanying color photographs and traits show typical specimens of the new cultivar at various stages of development as nearly true as it is possible to make in color reproductions.

The pictures were taken during May 2022 in Huelva, Spain.

DETAILED DESCRIPTION OF THE INVENTION

Figure 1A:
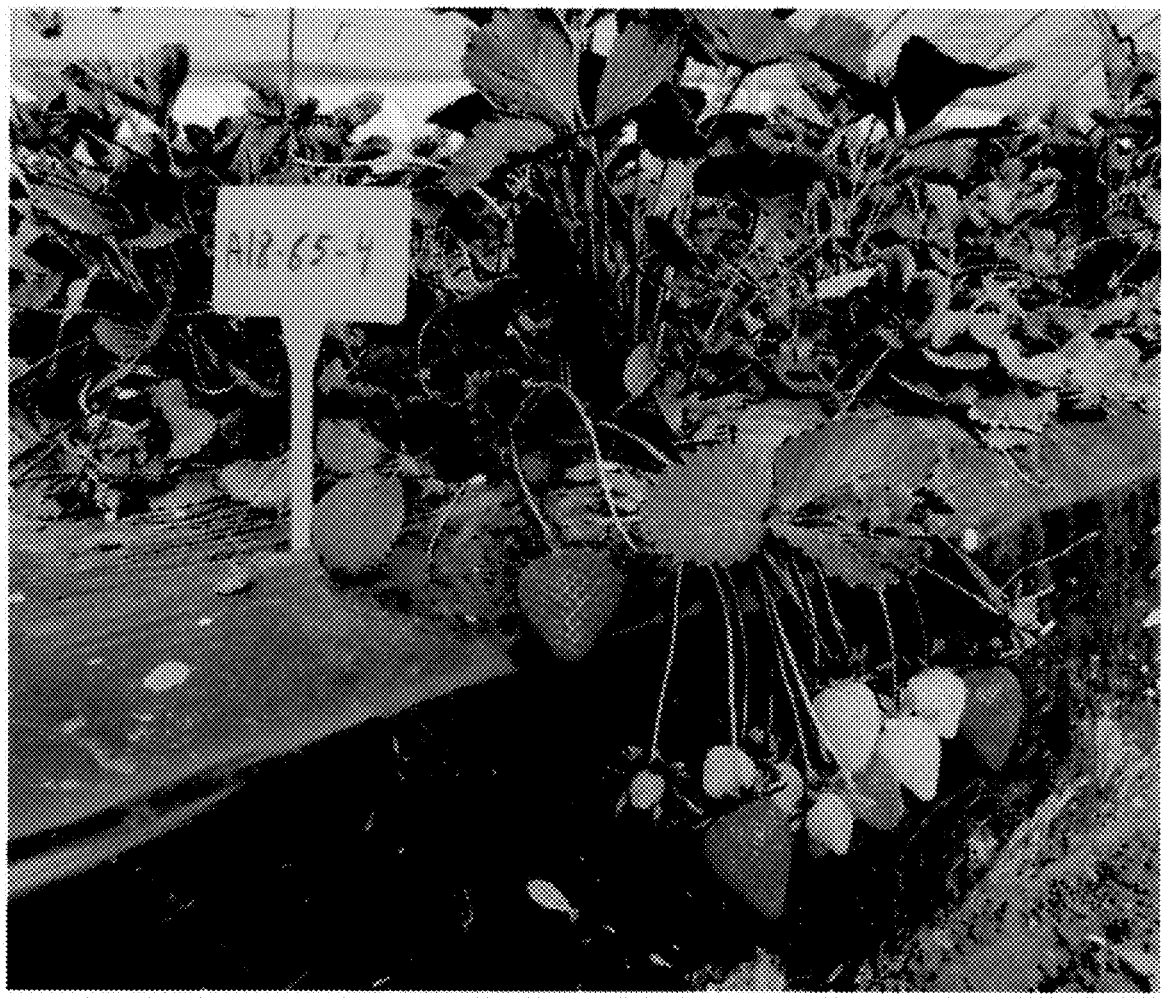
FIGS. 1A and 1B show overall plant habit including fruit at various stages of development.
Figure 1B:
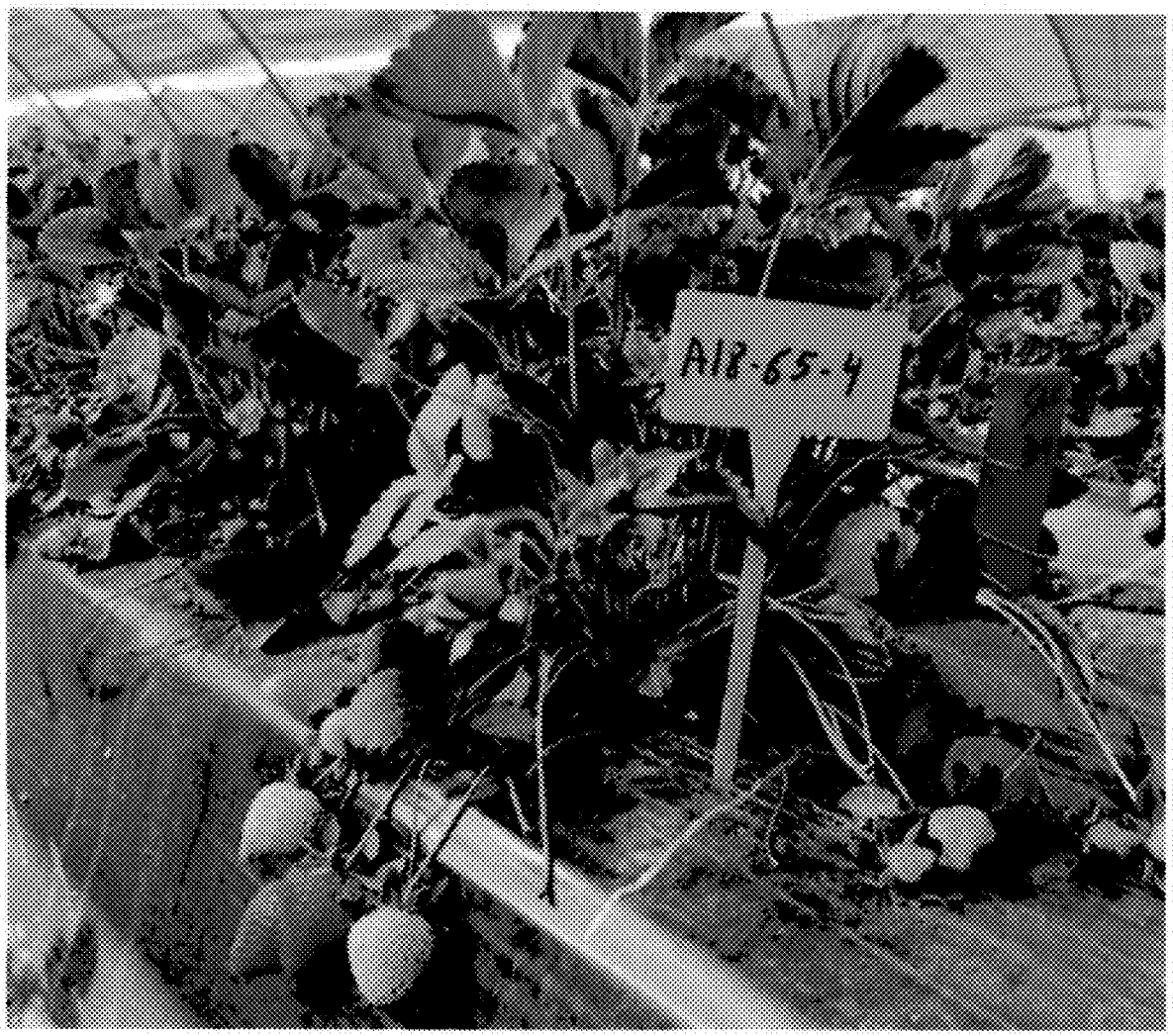
Figure 2A:
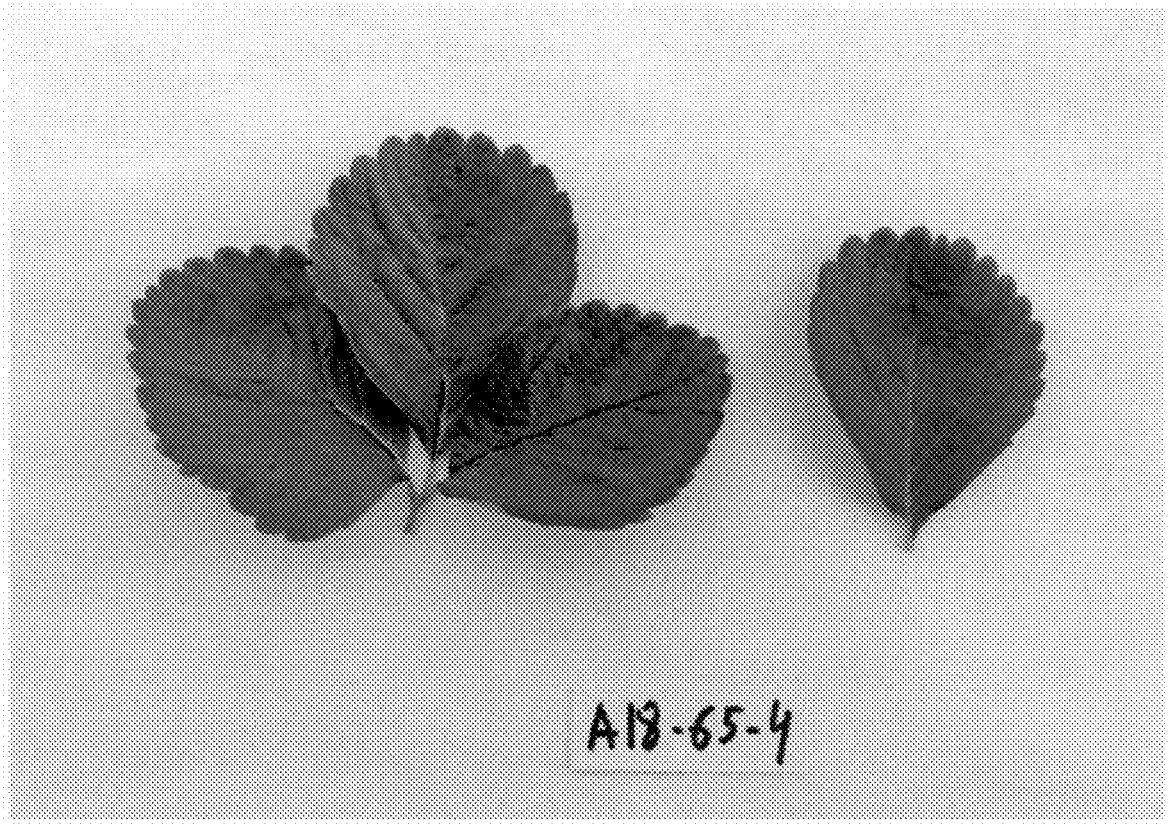
FIG. 2A shows the front side of a leaf with three leaflets.
Figure 2B:
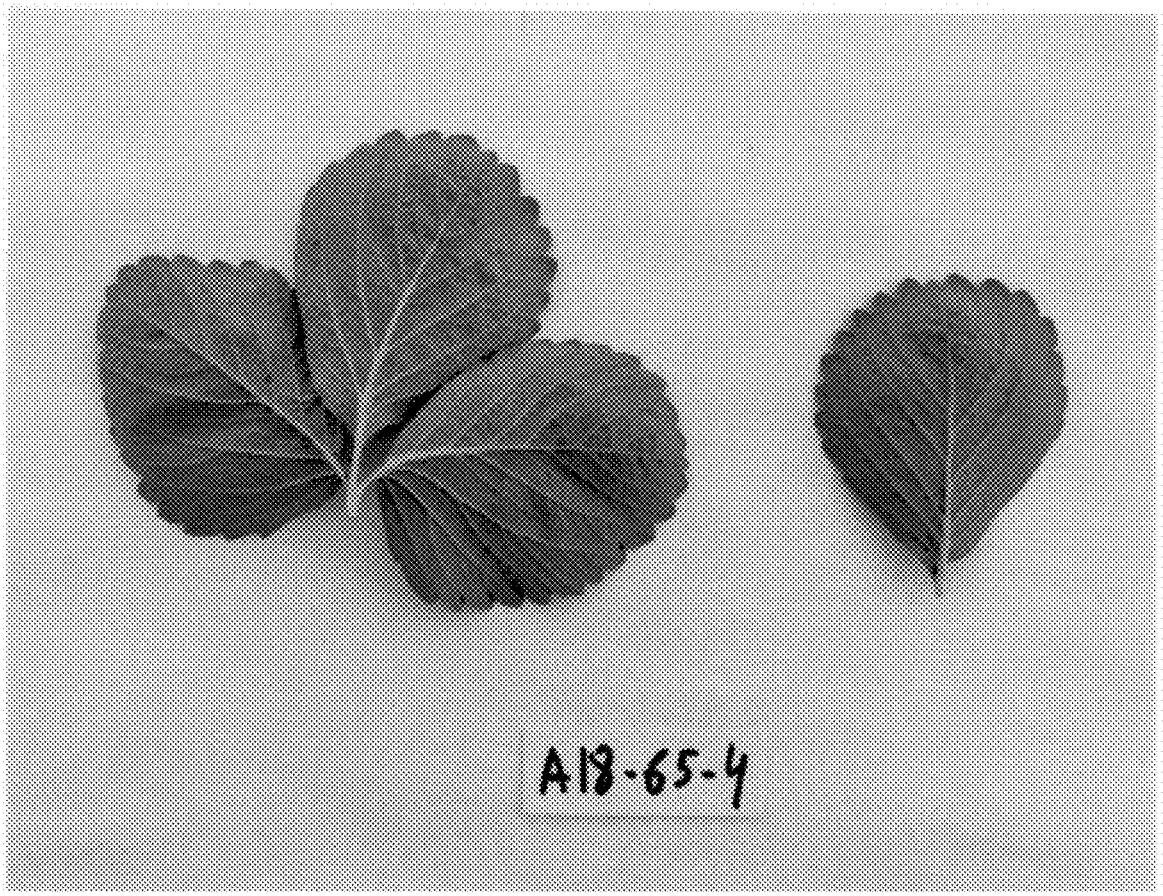
FIG. 2B shows the back side of the leaf.
Figure 3A:
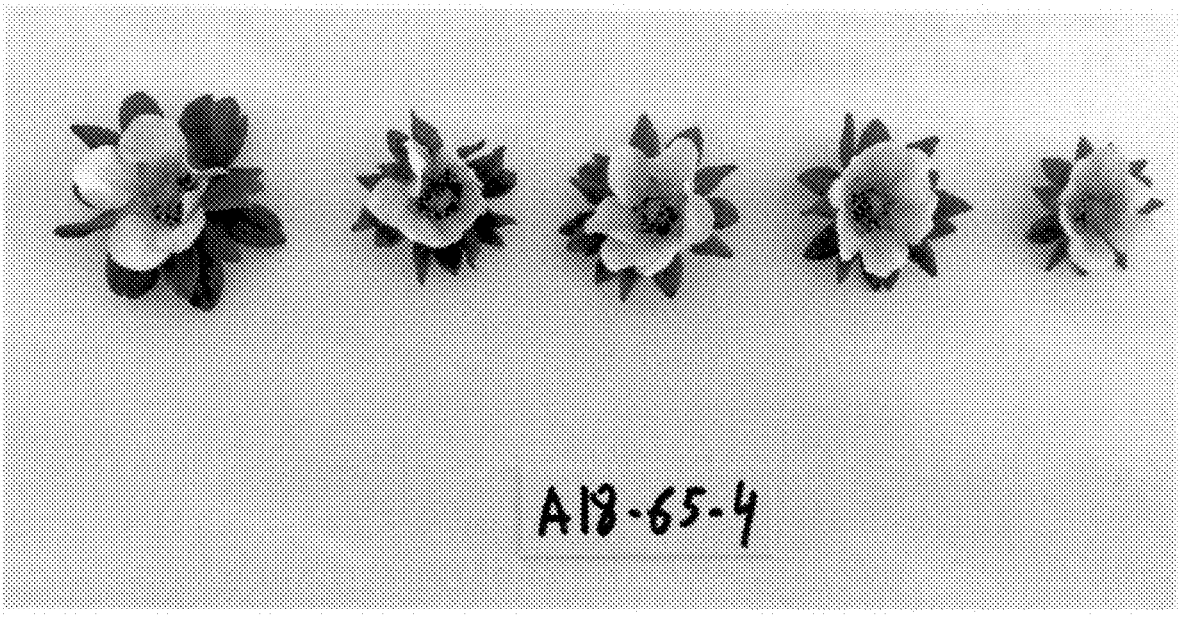
FIG. 3A shows flowers from the top.
Figure 3B:
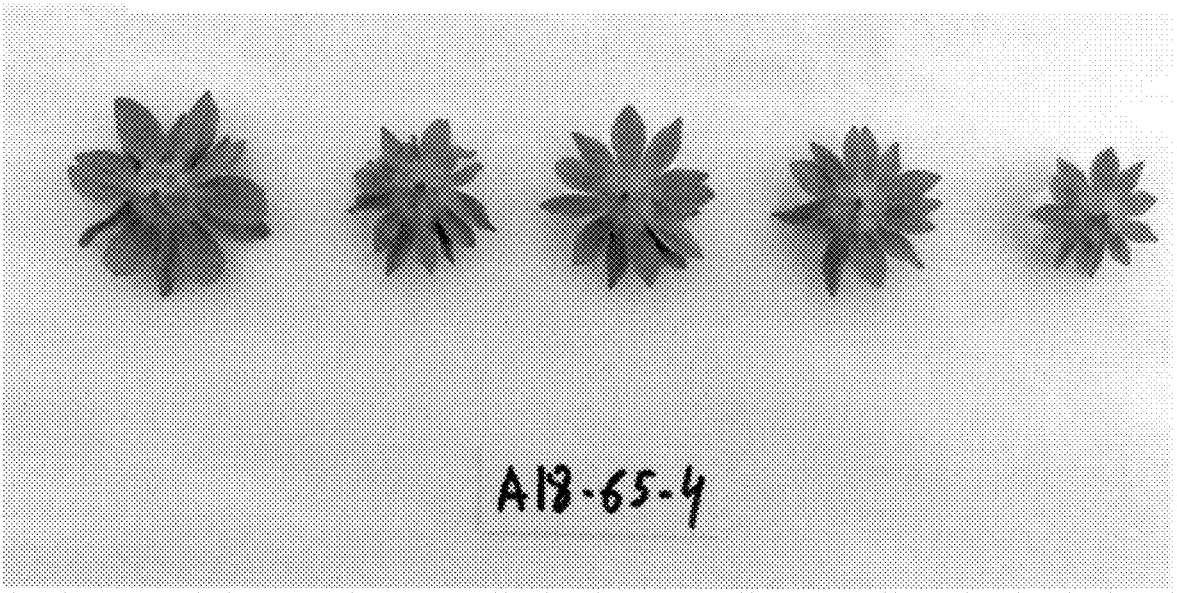
FIG. 3B shows flowers from the bottom.
Figure 4A:
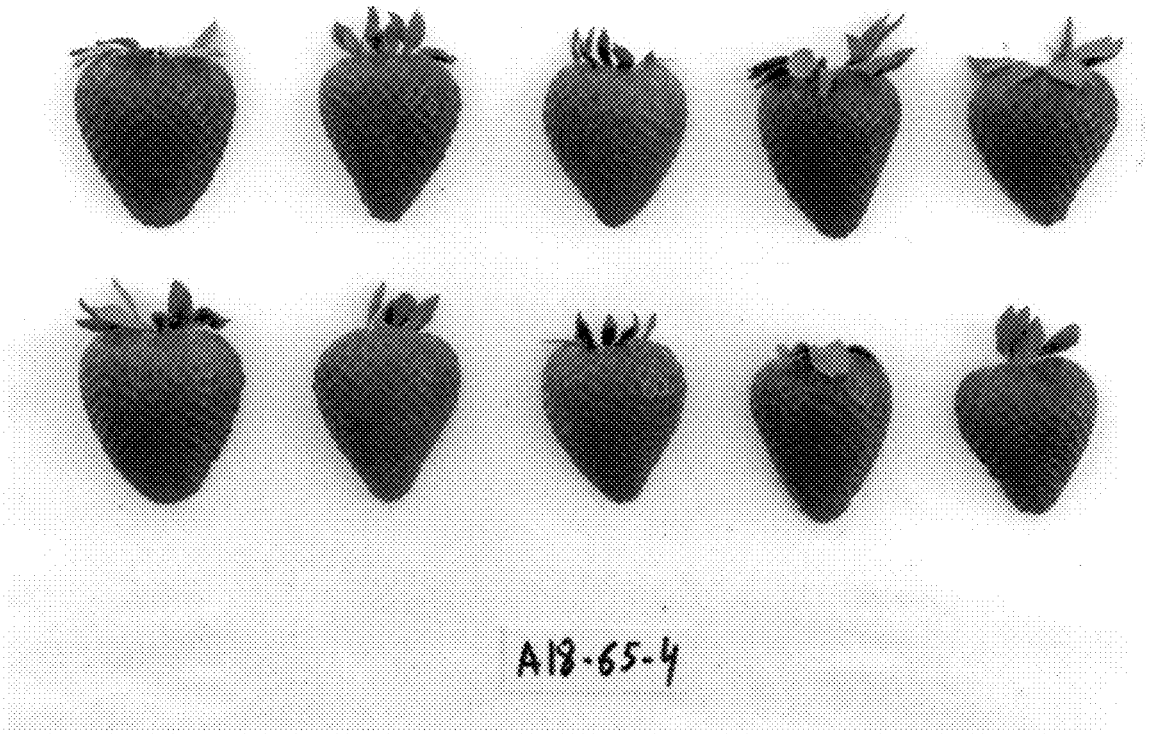
FIG. 4A shows the whole fruit.
Figure 4B:
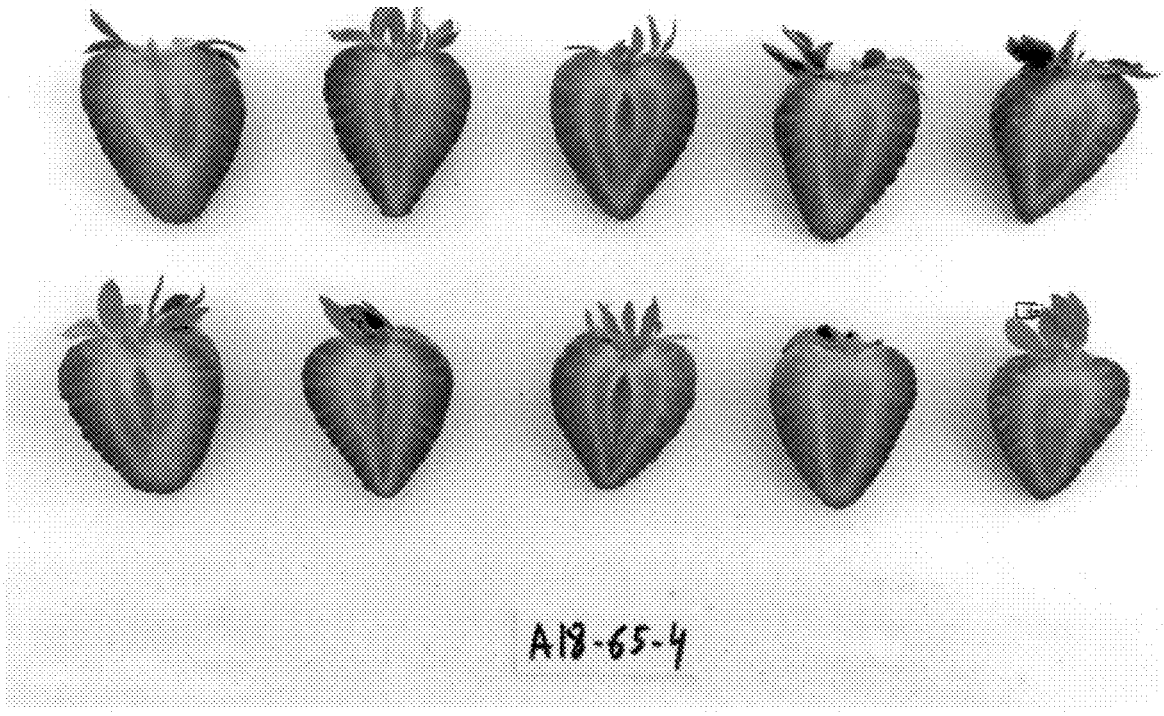
FIG. 4B shows the fruit in longitudinal cross-section.

This invention relates to a new and distinctive short-day variety named 'DUNA'. This variety is primarily adapted to the climate and growing conditions of the South of Spain (Huelva, Spain). However, this variety can be planted in any place of the world.

'DUNA' is a medium-vigorous plant, and produces fruits of a large size, with a conical shape and a medium red color. The fruit has an excellent quality with its high firmness is high and its moderate to high sweetness of 8.3° brix. Also, it is noteworthy that the new variety 'DUNA' has early flowering and ripening. The 'DUNA' variety produces a large amount of stolons which facilitate its multiplication.

The 'DUNA' variety is tolerant to the most frequent diseases in strawberry production, including those common to Huelva, Spain. Specifically, it is tolerant to powdery mildew (*Sphaerotheca macularis*), Phytophthora crown rot (*Phytophthora cactorum*), and charcoal rot (*Macrophomina phaseolina*).

The following traits in combination distinguish strawberry variety 'DUNA' from known strawberry variety, Fronteras (Table 1. General, Table 2. Leaf, Table 3. Runner (Stolon), Table 4. Inflorescence, and Table 5. Fruit, Table 6. Petiole, stipule and pedicel). A phenotypic comparison between the 'DUNA' variety and the comparator 'Fronteras' variety (U.S. Plant Pat. No. 26,709) is provided in Tables 1-6. The traits were measured in Huelva, Spain. The plant was 6 months old when measurements were taken in 2022 strawberry season (Confidence intervals (CI) are reported at $\alpha$=0.05 and were calculated assuming a Student's t-distribution. N =10). Fresh bare root plant was used for planting. Plants for the botanical measurements in the present application were grown as annuals. Any color references are made to The Royal Horticultural Society Colour Chart, 1995 Edition, except where general terms of ordinary dictionary significance are used. The yield and brix results in Table 7 come from a trial conducted in Huelva, Spain. The trial was a randomized complete block design with three repetitions and 40 plants per plot. It was cultivated under standard conditions of strawberry cultivation in Huelva, Spain.

The new variety 'DUNA' has clear differences with respect to the number of runners and the timing of flowering and ripening, when compared to the variety 'Fronteras.' The variety 'DUNA' has more runners (stolons) than 'Fronteras' and shows flowering and ripening earlier than the variety 'Fronteras.'

TABLE 1

General

| Characteristic | DUNA | Fronteras |
|---|---|---|
| Plant Growth Habit | Upright | Semi-upright |
| Day length | Short-day | Short-day |
| Density of foliage | Sparse | Sparse |
| Plant vigor | Medium | Medium |

TABLE 2

Leaf

| Characteristic | DUNA | Fronteras |
|---|---|---|
| Leaf: Variegation | Absent | Absent |
| Leaf: Blistering | Medium | Medium |
| Number of leaflets | 3 | 3 |
| Leaf size (length × width) | Medium (96 mm × 127 mm, ±5 × 7 mm) | Medium ( 90 mm × 123 mm ± 6 × 13 mm) |
| Terminal leaflet: relative length/width ratio (length × width) | Moderately longer than wide (67 mm × 54 mm, ±4 × 4 mm) | Moderately longer than wide (64 mm × 51 mm, ±6 × 6 mm) |
| Terminal leaflet: Shape of the base | Acute | Acute |
| Terminal leaflet: Margin | Crenate | Crenate |
| Leaf color of upper side | Medium green (RHS NN137A) | Light green (RHS 139A) |

TABLE 3

Runner (Stolon)

| Characteristic | DUNA | Fronteras |
|---|---|---|
| Number of runners (stolons) | Many | Medium |
| Stolon anthocyanin (color code) | Absent to very weak (RHS 145B) | Absent to very weak (RHS 146D) |

TABLE 4

Inflorescence

| Characteristic | DUNA | Fronteras |
|---|---|---|
| Number of flowers | Many | Many |
| Flower diameter | Large, 35 mm, ±3 mm | Large to medium, 31 mm, ±1 mm |
| Inflorescence position relative to foliage | Above | Above |
| Relative size of calyx relative to corolla | Larger | Larger |
| Stamen | Present | Present |
| Petal spacing | Touching | Touching to overlapping |
| Petal color of upper side | White (RHS 155B) | White (RHS 155C) |
| Petal length in relation to width (width × length) | Moderately longer, 11 mm × 13 mm, ±0.7 × 0.8 mm | Moderately longer to equal, 11 mm × 12 mm, ±0.4 × 0.6 mm |
| Color of calyx | RHS 143C | RHS 143A |
| Petal number per flower | 5 to 6 | 5 to 7 |
| Sepal number per flower | 10 to 12 | 12 to 14 |
| Number of stamen | 27 to 32 | 27 to 32 |
| Color and length of style | RHS 154A, 1.5 mm, ±0.1 mm | RHS 150C, 1.6 mm, ±0.1 mm |
| Color of ovary | Green | Green |
| Anther shape | Oval | Oval |
| Anther color | RHS 7A | RHS 7A |
| Anther length | 1.7 mm, ±0.1 mm | 1.6 mm, ±0.1 mm |
| Filament color | Green | Green |
| Filament length | 2.6 mm, ±0.3 mm | 2.4 mm, ±0.3 mm |

TABLE 5

| Fruit | | |
|---|---|---|
| Characteristic | DUNA | Fronteras |
| Fruit weight | 38 g, ±5.8 g | 36 g, ±4.9 g |
| Relative length/width ratio (length × width) | Moderately longer than wide (52 mm × 43 mm, ±3 × 2 mm) | Moderately longer than wide (55 × 39 mm, ±3 × 1 mm) |
| Relative fruit size | Large | Large |
| Predominant fruit shape | Conical | Conical |
| Difference in shape of terminal and other fruits | Slight | Slight |
| Color of surface | Medium red (RHS 44A) | Medium red (RHS 53A) |
| Color of flesh (excluding core) | Medium red (RHS 35A) | Medium red (RHS 42B) |
| Color of core | Light red (RHS 35B) | Light red (RHS 38C) |
| Evenness of surface | Even or very slightly uneven | Even or very slightly uneven |
| Fruit achene color | RHS 163B | RHS 166A |
| Width of band without achenes | Absent or very narrow | Absent or very narrow |
| Position of achenes | Slightly below surface | Below surface |
| Position of calyx attachment | Level with fruit | Level with fruit |
| Firmness | Firm | Medium |
| Cavity | Absent or small | Medium |
| Time of flowering | Very early | Early |
| Time of fruit ripening | Very early | Early |
| Remontancy (Reblooming) | Non-remontant | Non-remontant |

TABLE 6

| Petiole, stipule, and pedicel | | |
|---|---|---|
| Characteristic | DUNA | Fronteras |
| Petiole length | Medium, 174 mm, ±12 mm | Short, 138 mm, ±12 mm |
| Petiole attitude of hairs | Horizontal | Horizontal |
| Petiole diameter | 2.8 mm, ±0.1 mm | 3.1 mm, ±0.2 mm |
| Petiole color | RHS 144C | RHS 144C |

TABLE 6-continued

| Petiole, stipule, and pedicel | | |
|---|---|---|
| Characteristic | DUNA | Fronteras |
| Stipule anthocyanin coloration | Weak (RHS 144C) | Weak (RHS 144C) |
| Stipule length | 31 mm, ±3 mm | 36 mm, ±5 mm |
| Stipule width | 8 mm, ±1 mm | 7 mm, ±1 mm |
| Stipule pubescence | Sparse to medium | Sparse to medium |
| Pedicel attitude of hairs | Upwards | Upwards to slightly outwards |
| Pedicel color | RHS 144C | RHS 144C |

The phenotypic comparison between the 'DUNA' variety and the comparator 'Fronteras' variety (U.S. Plant Pat. No. 26,709) is shown in Tables 1-6. The yield and brix results in Table 7 come from a trial conducted in Huelva, Spain. The trial was a randomized complete block design with three repetitions and 40 plants per plot. It was cultivated under standard conditions of strawberry cultivation in Huelva, Spain.

TABLE 7

| Fruit production and Brix degrees data of the new variety 'DUNA' and 'Fronteras' | | | | | |
|---|---|---|---|---|---|
| Variety | PCP (g) | PCT (g) | PPT (%) | PPCT (%) | BRIX |
| DUNA | 308 | 1256 | 1194 | 95 | 8.3 |
| Fronteras | 225 | 1197 | 1153 | 96 | 8.8 |

Each value in Table 7 is the result of the average of three repetitions of 40 plants. PCP, early production (before March 31) in grams by plant; PCT, total commercial yield in grams by plant harvested; PPT, commercial yield in grams by first class fruit; PPCT, percentage of first class fruit over the total commercial yield; BRIX, Brix degrees.

The invention claimed is:

1. A new and distinct cultivar of strawberry plant named 'DUNA' having the characteristics substantially as described and illustrated herein.

* * * * *